(12) United States Patent
Bernasconi et al.

(10) Patent No.: US 6,193,959 B1
(45) Date of Patent: *Feb. 27, 2001

(54) LIGHT SCREENING COMPOSITIONS

(75) Inventors: Pierclaudio Bernasconi, Meyrin; Hans Ulrich Gonzenbach, Geneva, both of (CH)

(73) Assignee: Roche Vitamins Inc., Parsippany, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/834,345

(22) Filed: Apr. 16, 1997

Related U.S. Application Data

(63) Continuation of application No. 08/539,135, filed on Oct. 4, 1995, now abandoned.

(30) Foreign Application Priority Data

Oct. 14, 1994 (EP) .................................................. 94810601
Feb. 20, 1995 (EP) .................................................. 95102337

(51) Int. Cl.$^7$ ...................................................... A61K 7/42
(52) U.S. Cl. ........................................... 424/59; 424/70.9
(58) Field of Search ...................................... 424/59, 70.9

(56) References Cited

U.S. PATENT DOCUMENTS

| 4,387,089 | * | 6/1983 | DePolo ..................................... 424/59 |
| 5,053,290 | | 10/1991 | Canivenc et al. . |
| 5,403,944 | * | 4/1995 | Frater et al. ........................... 556/441 |
| 5,415,854 | * | 5/1995 | Forestier et al. ....................... 424/59 |
| 5,624,663 | * | 4/1997 | Deflandre et al. ..................... 424/59 |

FOREIGN PATENT DOCUMENTS

| 642 536 | 4/1984 | (CH) . |
| 305 059 B1 | 3/1989 | (EP) . |
| 358 584 | 3/1990 | (EP) . |
| 2 642 967-A1 | 8/1990 | (FR) . |
| WO 92/20690 | 11/1992 | (WO) . |
| WO 93/10745 | 6/1993 | (WO) . |
| WO 94/06404 | 3/1994 | (WO) . |

OTHER PUBLICATIONS

Derwent Abstract of WO 92/20690.
Derwent Abstract of EP 358 584.
Derwent Abstract of FR 2 642 967–A1.
Derwent Abstact of CH 642 536.

* cited by examiner

Primary Examiner—Margaret G. Moore
(74) Attorney, Agent, or Firm—Mark E. Waddell; Stephen M. Haracz; Bryan Cave LLP

(57) ABSTRACT

Photostable, cosmetic light-screening compositions for the protection of the human epidermis and the hair against the ultraviolet rays of wavelengths between 290 and 400 nm comprising, in a cosmetically acceptable vehicle containing at least one fatty phase, about 0.5 to about 5%, in particular about 1 to about 4% by weight, of a dibenzoylmethane type UV-A screening agent and at least about 0.1% to about 20%, in particular about 0.5 to about 15% by weight, of a polymer UV-B filter of the benzylidene malonate silicone type

2 Claims, No Drawings

LIGHT SCREENING COMPOSITIONS

This is a continuation of U.S. application Ser. No. 08/539,135, filed Oct. 4, 1995, abandoned.

The invention relates to photostable, cosmetic light-screening compositions for the protection of the human epidermis and the hair against the ultraviolet rays of wavelengths between 290 and 400 nm.

In particular, it relates to such compositions which comprise, in a cosmetically acceptable vehicle containing at least one fatty phase, about 0.5 to about 5%, in particular about 1 to about 4% by weight, of a dibenzoylmethane type UV-A screening agent and at least about 0.1% to about 20%, in particular about 0.5 to about 15% by weight, of a polymer UV-B filter of the benzylidene malonate silicone type exhibiting an organosiloxane having at least one unit of the general formula $$\frac{O_{3-a}Si(R)_a}{2}-\underset{\alpha}{C}=|=\underset{\beta}{CH} \atop (CR_2^1)_n-O-C_6R_2^2H_2-CH=C-[C(O)OR^3]_2 \tag{I'}$$

or $$\frac{O_{3-a}Si(R)_a}{2}-CR^1-|-|-CHR^1 \atop (CR_2^1)_n-O-C_6R_2^2H_2-CH=C-[C(O)OR^3]_2 \tag{II'}$$

wherein the radical $$\overset{R^1}{|}$$

is either bound to the $C_\alpha$ atom and the radical $$\overset{|}{(CR_2^1)_n}-$$

is bound to the $C_\beta$ atom of the double bond in (I') or in the corresponding single bond in (II'), or vice versa, any other units present in the said siloxanes being those represented by the general formula $$R''_b SiO_{\frac{4-b}{2}} \tag{III}$$

wherein R represents a $C_{1-8}$ alkyl or an aryl group, $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group, R" represents a hydrogen atom, a monovalent $C_{1-8}$ hydrocarbon or halogenated hydrocarbon group, a has a value of 0, 1 or 2, b has a value of 0, 1, 2 or 3 and n has a value of from 1 to 6, provided that the $$-C=|=CH \atop -(CR_2^1)_n-O-$$

-continued
or the $$-CR^1-|-|-CHR^1 \atop -(CR_2^1)_n-O-$$

groups and the two $R^2$ groups are linked to the aromatic ring ($C_6$ . . . ) at the para- and both meta-positions in relation to the group $-CH=C[C(O)OR^3]_2$, and the two vertical strokes designate either the alkylene derivative $$Si-\underset{\alpha}{C}=\underset{\beta}{CH}-(CR_2^1)_n \ldots \atop \overset{R^1}{|}$$

or the alkylidene derivative $$Si-\underset{\alpha}{C}=\underset{\beta}{CHR^1} \atop \overset{(CR_2^1)_n \ldots}{|}$$

in case of formula (I'), or the saturated derivative with a linear chain $$Si-CR^1-CHR^1-(CR_2^1)_n \ldots \atop \overset{R^1}{|}$$

or the saturated derivative with a branched chain $$Si-CR^1-CHR_2^1 \atop \overset{|}{(CR_2^1)_n \ldots}$$

in case of formula (II'), the weight ratio of the silicone to the dibenzoylmethane derivative being not less than about 0.1, preferably not less than about 1.0, and not more than about 25, preferably not more than about 8 to 10.

An alternative designation for the subject matter of compounds I' and II' is thus $$\frac{O_{3-a}Si(R)_a}{2}-U-O-C_6R_2^2H_2-CH=C-[C(O)OR^3]_2 \tag{I}$$

or $$\frac{O_{3-a}Si(R)_a}{2}-V-O-C_6R_2^2H_2-CH=C-[C(O)OR^3]_2 \tag{II}$$

wherein

U is $-C=CHR^1 \atop \overset{|}{(CR_2^1)_n}-$ or $-C(R^1)=CH-(CR_2^1)_n-$ and

-continued

V is 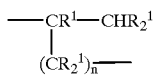

or

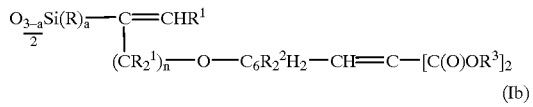

Formula I encompasses thus, as pointed out above, the alkylidene derivative Ia and the alkylene derivative Ib:

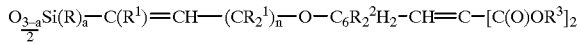

(Ia)

$O_{3-a}Si(R)_{\frac{a}{2}}$—C≡CHR$^1$ (CR$_2^1$)$_{\overline{n}}$—O—C$_6$R$^2_2$H$_2$—CH═C—[C(O)OR$^3$]$_2$ (Ib)

$O_{3-a}Si(R)_{\frac{a}{2}}$—C(R$^1$)═CH—(CR$_2^1$)$_{\overline{n}}$—O—C$_6$R$^2_2$H$_2$-CH═C—[C(O)OR$^3$]$_2$ The preparation and the properties of these benzylidene malonate silicone types are described in WO 92/20690 of Nov. 26, 1992.

The ratio of the alkylene to the alkylidene derivative is not critical, and is normally between about 5- about 50%:about 95–50% w/w, in particular about 20–30:80–70% w/w, or in the case of the saturated derivatives, the linear derivative is the predominant derivative.

Formula II encompasses the saturated linear (IIa) and saturated branched (IIb) derivatives:

(IIa)

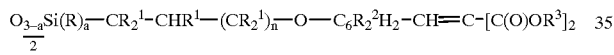

(IIb)

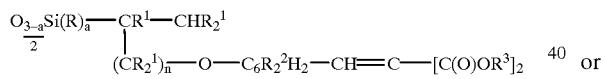

The preparation and properties of such benzylidene malonate silicone compounds is described in EP 358 584 (U.S. Pat. No. 5,053,290) and FR 2 642 967-A1 (U.S. Pat. No. 5,415,854).

The suitable dimensions for the various parameters of the definition of the above captioned formula III are equally derivable from WO 92/20690. Thus, in the general formulae I and II the radicals can be defined as follows:

R may be for example methyl, ethyl, butyl or phenyl.

R" is hydrogen or a monovalent hydrocarbon or halogenated hydrocarbon group having up to 8 carbon atoms, for example alkyl, alkenyl, aryl, alkaryl, aralkyl and also halogen substituted alkyl, alkenyl, aryl, alkaryl and aralkyl are such groups. Particular examples include methyl, ethyl, vinyl, phenyl, tolyl, ethylphenyl, dimethylphenyl, benzyl, phenethyl and 3,3,3-trifluoropropyl, etc.

$R^3$ denotes alkyl groups having up to 5 carbon atoms, as for example methyl, ethyl, propyl, isopropyl, butyl, secondary butyl, isobutyl, pentyl and neopentyl, etc.

Examples for the $C_{1-5}$ alkyl radicals of $R^1$ and $R^2$ are as given above. Suitable radicals $OR^1$ are methoxy, ethoxy, propoxy, isopropoxy, etc. From the above listing, it can also be deduced that the alkyl and the alkoxy radicals may in the present context represent straight-chain and branched radicals.

It is preferred that at least 80% of all R and R" groups are methyl groups, most preferably substantially all R and R" groups are methyl groups. It is also preferred that $R^1$ is either hydrogen, methyl or ethyl, most preferably hydrogen. Preferably each $R^2$ group is hydrogen or one $R^2$ group is a hydrogen, while the other one is an alkoxy group, preferably methoxy or ethoxy. $R^3$ is preferably methyl or ethyl. In addition, a is preferably 1 while b is preferably 2, making the organosilicon compound a substantially linear or cyclic diorgano-siloxane polymer. However, if the diorganosiloxane—see, e.g. Table 1, the second formula—is a substantially linear polymer at least two end blocking units must be present, thus requiring the presence of 2 units in which a has a value of 2, two units in which the value of b is 3 or one unit wherein a is 2 and one unit in which b is 3. n is preferably 1, 2 or 3. Suitable preferred polymers have therefore either the general formula

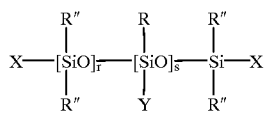

or

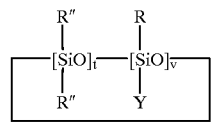

wherein R and R" are as defined above, X denotes a group Y or a group R" and Y denotes an alkylene group of the formula

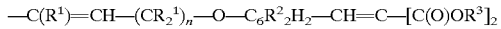

or the corresponding alkylidene derivative in case of formula (I), or, in case of formula (II), one of the groups

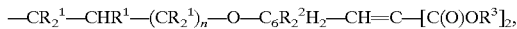

or

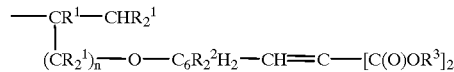

In the above captioned formulae, r has a value of from 0 to 130, s has a value of from 0 to 20, whereby at least one X denotes Y in the case that s=0; t has a value of from 0 to 10, v has a value of from 1 to 10 and v+t has a value of at least 3, and $R^1$, $R^2$ and $R^3$ are as above.

In the substituent Y of the organosilicon compounds, the above captioned alkylene group

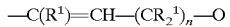

or the corresponding above captioned alkylidene derivative, or the groups

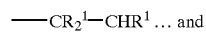

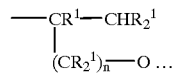

may occupy the meta-position or the para-position of the aromatic ring ($C_6$ . . . ) in relation to the group —CH═C[C(O)OR$^3$]$_2$.

Preferably the para-position is thus occupied. The groups $R^2$ occupy the remaining two positions out of the para- and meta-positions in relation to the group —CH=C[C(O)OR$^3$]$_2$. Examples of preferred substituents Y thus include

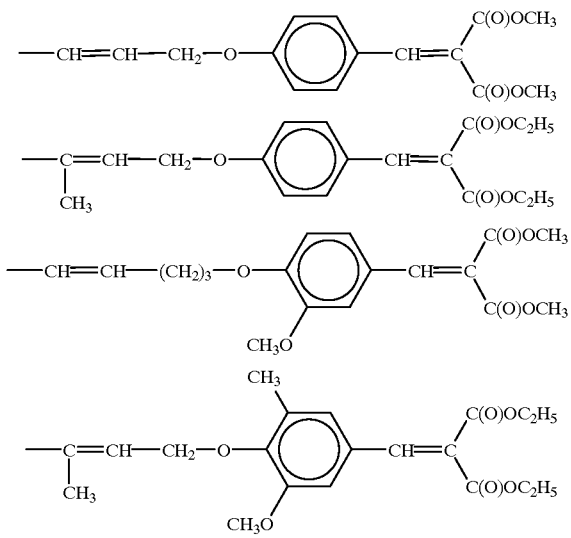

or the corresponding alkylidene derivatives, or the saturated linear structures, such as:

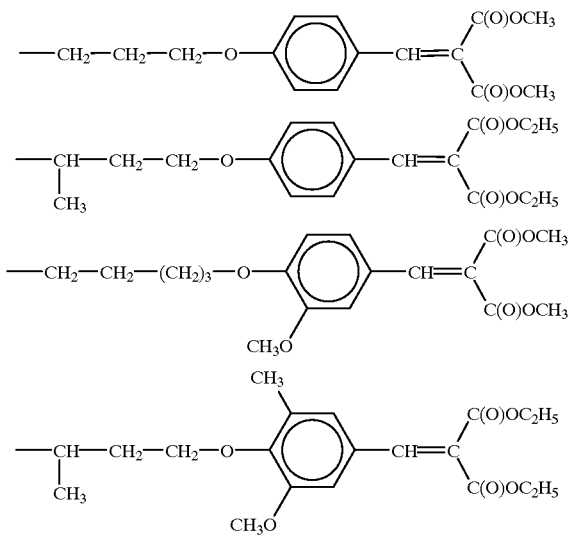

or the corresponding saturated branched derivatives, namely those carrying the structure

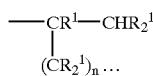

The material organosilicon compounds have at least one unit falling within the general formulae (I) or (II), preferably at least 2. Suitable organosilicon compounds are polymeric materials which may be homopolymers consisting only of such units (I) or (II), or they may be copolymers containing both units (I) or (II) and units having the general formula (III). The organosilicon compounds may vary from freely flowing liquids to highly viscous gum-like materials or resinous solids. Preferred, at least for cosmetic applications, are the liquid substantially linear organosiloxane homopolymers and copolymers, for example those having a viscosity (in c St) of from 100 to 20000 mm$^2$/s, more preferably 500 to 5000 mm$^2$/s as these are more easily mixed with other ingredients to make cosmetic compositions and as they will spread more easily onto the skin.

Organosilicon compounds which are especially preferred are those wherein the number of units (I) or (II) is limited to a maximum of 20% to 25% of the total number of siloxane units in the molecule. For maximum efficiency in its U.V. absorbing property it is preferred that the number of units (I) or (II) be limited to 10% to 12% or less of the total. The units of formula (I) or (II) may be distributed randomly in an organosiloxane polymer, they may be end-blocking units of the polymer or they may be located at the end of the poly-mer and pending in chain of the polymer at the same time. Units of the general formula (I) or (II) are conveniently situated at the end of the organosiloxane polymer forming one or more endblocking units of the polymer. In one class of the preferred organosilicon compounds which are substantially linear polyorganosiloxane polymers, both end-blocking units have a structure represented by the general formula (I) or (II), while all other units are according to the general formula (III). The preferred organosilicon compounds have four units of the formula (I) or (II) and a larger number of units according to the general formula (III), e.g. 6 to 130, especially 8 to 80.

The organosilicon compounds are themselves effective in absorbing ultra violet radiation in the erythemic region (290–320 nm) which makes them particularly suitable for use in cosmetic sunscreen preparations where absorption in the UV-B region is particularly desirable. Most preferred for this application are those that have a maximum absorbance at 300–320 nm.

As far as the UV-A light screen agent of the novel combinations is concerned, the preferred compound is 4-tert. butyl-4'-methoxy-dibenzoylmethane, as disclosed e.g. in U.S. Pat. No. 4,387,089 or CH-Patent 642 536.

Other suitable compounds of this particular type are: 2-methyldibenzoylmethane, 4-methyl-dibenzoyl-methane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxydibenzoylmethane, 2-methy-5-tert-butyl-4'-methoxydibenzoylmethane, 2,4-dimethyl-4'-methoxydibenzoylmethane and 2,6-dimethyl-4-tert-butyl-4'-methodydibenzoylmethane.

The function of the polymer filter containing formula I units is not only to provide the necessary so-called A+B total block in the final composition, in as far as the absorption of the UV-radiation is concerned, but also to photostabilize the involved UV-A screening agents, i.e. to guarantee a constant protection during prolonged exposure to the UV-light. This way, if a repeated application of the cosmetic formulation at various intervals is required, these intervals can be extended.

The present invention relates thus also to a process for stabilising dibenzoylmethane UV-A screening agents with respect to UV radiation of wavelengths between 290 and 400 nm, characterised in that 0.1 to 20% by weight of the polymer filter is added to 0.5 to 5% by weight of the dibenzoylmethane UV-A screening agent, the weight ratio of the silicone to the dibenzoylmethane derivative being not less than 0.1 and not more than 25.

The desired stabilization of the material UV-A filters is easily established by strictly parallel experiments with the respective UV-A filters and the novel combinations using an appropriately equipped Xenon lamp as a solar simulator. Irradiated are standard preparations of the investigated products, e.g. solutions in cosmetic solvents, the resulting sunscreen being spread on quartz plates. The stabilizing effect is directly correlated to the difference in absorbance at $I_{max}$ before and after the irradiation. For an satisfactory effect, the structures of I and II are essential.

Even a slight variation of the structure in the molecules I and II leads to an unsatisfactory respective stabilization; under slight variation there is understood the "removal" of an ester group in I and II, thus resulting in cinnamates (namely the benzylidene acetates . . . —CH=C—C(O)OR$^3$), viz. EP 305059.

Both components of the present combination of the light-screening agents are lipophilic. The cosmetic formulations contain thus at least one fatty phase, and the formulations can consequently present themselves in the form of emulsions, lotions or gels.

Suitably the cosmetic screening composition takes the form of an oil, a lotion, a gel, a solid stick, an emulsion, e.g. cream, milk or of a vesicular dispersion of ionic or nonionic amphiphilic lipids, an aerosol, a spray, a foam, a powder, a shampoo, a hair conditioner or lacquer or a make-up, etc.

The usual solvents known to the skilled practitioner can be used for the preparation of these forms, e.g. oils, waxes, alcohols, polyols, etc. The preferred agents are fatty acids, esters, fatty alcohols, but also ethanol, isopropanol, propylene glycol, glycerine, etc.

The cosmetic formulations may contain further adjuvants, e.g. further solvents, thickeners, emollients, emulsifiers, humectants, tensides, preservatives, antifoams, fragrances, oils, waxes, lower polyols and monohydric alcohols, propellants, silicones, colourings and pigments, etc.

The compositions may also contain further water-soluble or lipophilic UV screening agents.

Other UV-B-filters may also be incorporated. Examples are given in U.S. Pat. No. 4,387,089 mentioned above. Particularly in case of emulsions, such UV filters may, naturally, also be water-soluble derivatives. As still further suitable UV-B filters, microfine pigments, such as the usual micropigments of metal oxides may be used.

In case of protection of the hair, the suitable formulations are shampoos, conditioners, lotions, gels, emulsions, dispersions, lacquers, etc.

The preparation of all these formulations is well known to the skilled artisan in this field.

Examples of preferred polysiloxanes used for the present purpose are the ones of Table I below.

Further suitable polysiloxanes are those of Examples 3 to 6 of WO 92/20690, and also the product of Comparative Example 1 of WO 92/20690, the latter material representing a product encompassed by Formula II above.

Table I

Illustrative Compounds and Formulae

The first column relates to the material Example of WO 92/20690 dealing with the preparation of products of this type.

| 4 | s = ca. 4 | r = ca. 60 | $R^2$ = H (most preferred, "Polysiloxane A") |
| 4 | s = ca. 15 | r = ca. 127 | $R^2$ = H |
| 4 | s = ca. 15 | r = ca. 116 | $R^2$ = H |

-continued

| 4 | s = ca. 11 | r = ca. 51 | $R^2$ = H |
| 4 | s = ca. 4 | r = ca. 60 | $R^2$ = OMe |
| 4 | s = ca. 15 | r = ca. 127 | $R^2$ = OMe |
| 4 | s = ca. 15 | r = ca. 116 | $R^2$ = OMe |
| 4 | s = ca. 11 | r = ca. 51 | $R^2$ = OMe |

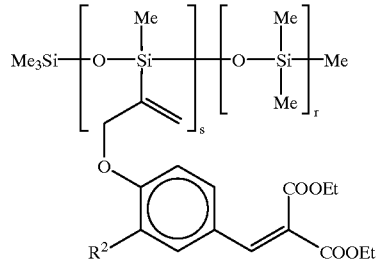

| 3 | r = ca. 7 | $R^2$ = H |
| 3 | r = ca. 7 | $R^2$ = OMe |

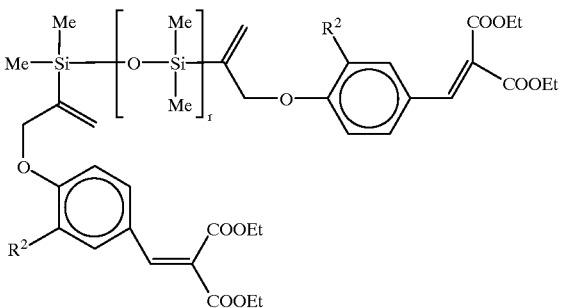

The above compounds contain ca. 20% of the alkylene isomers; their preparation can be illustrated as follows:

A. 39.84 g of {[4-(2-propynyloxy)phenyl]methylene}-diethyl ester were dissolved in 100 g of toluene and heated under nitrogen to about 70° C. 39.96 g of a hydrosiloxane having a degree of polymerisation of 8 and 25 mpc (mole %) SiH groups (9.7% SiH) were then added dropwise after a platinum complex was also added, giving $10^{-4}$ mole of Pt per mole of SiH of the hydrosiloxane. The mixture was heated to reflux and maintained until all SiH had disappeared of the infrared spectroscopic analysis. It was then allowed to cool to room temperature. The toluene was then evaporated to leave after washing 60.5 g of a brown, viscous polymer having the average structure

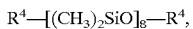

wherein R has the formula

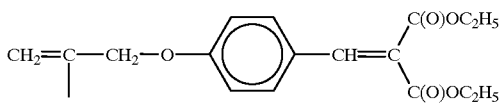

Only 0.34% by weight of the total reaction product of unreacted {[4-(2-propynyloxy)phenyl]methylene}-diethyl ester was present in the end product.

B. 13.28 g of {[4-(2-propynyloxy)phenyl]methylene}-diethyl ester were dissolved in 75 g of toluene and heated under nitrogen to about 70° C. 44 g of a hydrosiloxane having a degree of polymerisation of 65 and 6 mpc SiH groups (2.36% SiH) were then added dropwise after a platinum complex was also added, giving $10^{-4}$ mole of Pt per mole of SiH of the hydrosiloxane. The mixture was heated to reflux and maintained until all SiH had disappeared of the infrared spectroscopic analysis. It was then allowed to cool to room temperature. The toluene was then evaporated to leave after washing 52 g of a brown, viscous polymer having the average structure

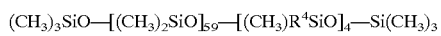

wherein $R^4$ has the formula

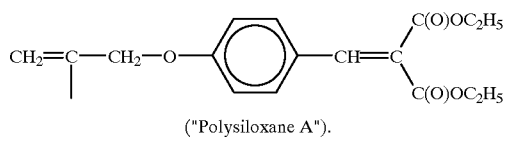

("Polysiloxane A").

EXAMPLES

1. A sunscreen cream is prepared with the following ingredients:

| | % (w/w) |
|---|---|
| A) Stearic acid (octadecanoic acid) | 10.0 |
| Butylmethoxy dibenzoylmethane | 2.0 |
| (1-[4-(1,1-dimethylethyl)phenyl]-3-(4-methoxyphenyl)-1,3-propanedione) | |
| (sold under the trade name PARSOL 1789 by Givaudan-Roure S.A.) | |
| Glyceryl mono myristate | 5.0 |
| (tetradecanoic acid ester with 1,2,3-propanetriol) | |
| Cetyl alcohol ((hexadecanol) | 2.0 |
| Coco-caprylate/caprate | 10.0 |
| (Mixture of esters of coconut alcohol and n-octanoic acid and n-decanoic acid) | |
| (sold under the trade name CETIOL LC by Henkel) | |
| Polysiloxane A | 10.0 |
| Dea Cetylphosphate | 3.0 |
| (Diethanolamine salt of hexadecyl phosphate) | |
| (sold under the trade name AMPHISOL by Givaudan-Roure S.A.) | |
| EDTA $Na_2$ (disodium ethylenediamine tetra acetic acid) | 0.1 |
| B Deionized water | 51.0 |
| Propyleneglycol (1,3-propanediol) | 6.0 |
| Mixture of parabens in phenoxyethanol | 0.6 |
| (Mixture of methyl, ethyl, propyl and butyl esters of 4-hydroxy benzoic acid) | |
| (sold under the trade name Phenonip ® by Nipa Laboratoires Ltd.) | |
| C Conventional fragrance | 0.3 |

2. A suncreen lotion is prepared with the following ingredients:

| | % (w/w) |
|---|---|
| A Glyceryl mono myristate | 5.0 |
| Cetyl alcohol | 2.0 |
| Butylmethoxy dibenzoylmethane | 1.0 |
| Isopropyl myristate (2-methylethyl tetradecanoate) | 7.0 |
| Oleyl alcohol (octadecanol) | 3.0 |
| Polysiloxane A | 5.0 |
| Dea Cetylphosphate | 3.0 |
| EDTA $Na_2$ | 0.1 |
| B Deionized water | 67.0 |
| Propyleneglycol | 6.0 |
| Mixture of parabens in phenoxyethanol 0.6 | |
| C Fragrance | 0.3 |

3. A suncreen lotion is prepared with the following ingredients:

| | % (w/w) |
|---|---|
| A Glyceryl mono stearate | 4.0 |
| Butylmethoxy dibenzoylmethane | 1.0 |
| Cetyl alcohol | 1.0 |
| Coco-caprylate/caprate | 6.0 |
| Polysiloxane A | 10.0 |
| Potassium cetyl phosphate (potassium salt of hexadecyl phosphate) | 2.0 |
| (sold under the trade name AMPHISOL K by Givaudan-Roure S.A.) | |
| EDTA $Na_2$ | 0.1 |
| B Deionized water | 59.36 |
| Carbomer (1% dispersion in water, homo polymer of acrylic acid crosslinked with an allyl ether of sucrose) | 10.0 |
| (sold under the trade name Carbopol 981 ® by B.F. Goodrich) | |
| Propyleneglycol | 5.0 |
| Potassium hydroxide, 10% solution | 0.64 |
| Mixture of parabens in phenoxyethanol | 0.6 |
| C Fragrance | 0.3 |

4. A water in silicone cream (a W/O formulation) is prepared with the following ingredients:

| | % (w/w) |
|---|---|
| A Butylmethoxy dibenzoylmethane | 1.0 |
| $C_{12/15}$ alkyl benzoate (mixture of dodecyl & pentadecyl benzoate) | 5.0 |
| (sold under the trade name FINSOLV TN by Finetex Corp.) | |
| Silicone oil (copolyol dimethicone and cyclomethicone) | 10.0 |
| (sold under the trade name DC-3225 by Dow Corning) | |
| Silicone oil (mixture of cyclomethicone and dimethiconol) | 10.0 |
| (sold under the trade name DC-1401 by Dow Corning) | |
| Polysiloxane A | 10.0 |
| EDTA $Na_2$ | 0.1 |
| B Deionized water | 56.0 |
| Sodium chloride | 4.0 |
| Propyleneglycol | 3.0 |
| Mixture of parabens in phenoxyethanol | 0.6 |
| C Fragrance | 0.3 |

In the same way, the Polysiloxane A can be replaced in the above formulations by the compound of Comparative Example 1 of WO 92/20690.

What is claimed is:

1. A photostable, cosmetic light-screening composition comprising:

a) a cosmetically acceptable vehicle containing at least one fatty phase;

b) about 0.5 wt % to about 5 wt % of a dibenzoylmethane type UV-A screening agent; and c) at least about 0.1 wt % to about 20 wt % of a photostabilizing benzylidene malonate silicone having formula:

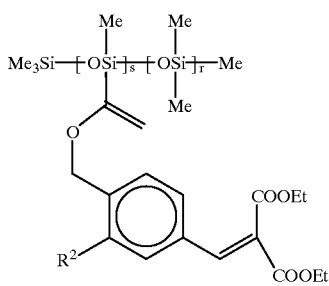

wherein:

R² is hydrogen or methoxy; and wherein r and s are selected from the following combinations: when r is 60, s is 4; when r is 127, s is 15; when r is 116, s is 15; and when r is 51, s is 11.

2. A photostable, cosmetic light-screening composition comprising:

a) a cosmetically acceptable vehicle containing at least one fatty acid phase;

b) about 0.5 to about 5% of a dibenzoylmethane UV-A screening agent; and c) at least about 0.1% to about 20 wt % of a photostabilizing benzylidene malonate silicone polymer having the following formula:

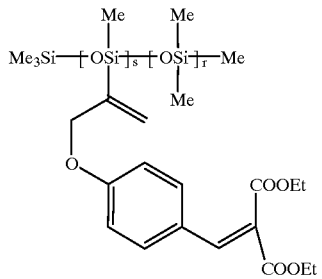

wherein r is 60, s is 4, and the weight ratio of the dibenzoylmethane to the benzylidene malonate silicone polymer is about 1:5.

* * * * *